US006576449B2

(12) United States Patent
Clark et al.

(10) Patent No.: US 6,576,449 B2
(45) Date of Patent: Jun. 10, 2003

(54) MICROBIAL PRODUCTION OF EPOXIDES

(75) Inventors: Thomas R. Clark, Lakewood, CO (US); Francisco F. Roberto, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/805,795

(22) Filed: Mar. 12, 2001

(65) Prior Publication Data

US 2002/0168733 A1 Nov. 14, 2002

(51) Int. Cl.[7] .............................. C12P 7/00; C12N 1/20
(52) U.S. Cl. ..................... 435/132; 435/252.1; 435/822
(58) Field of Search .............................. 435/252.1, 822, 435/132

(56) References Cited

U.S. PATENT DOCUMENTS 4,347,319 A * 8/1982 Hou et al. .................. 435/123
5,032,523 A * 7/1991 Amano et al. .............. 435/280
5,084,583 A * 1/1992 Rozen et al. ............... 549/524
5,863,789 A * 1/1999 Komatsu et al. ............ 435/262

OTHER PUBLICATIONS

Ascon–Cabrera et al. Appl. Environ. Microbiol. Jun. 1993, vol. 59, No. 6, pp. 1717–1724.*

Carrea G. Trends in Biotechnology,. 1984, vol. 2, No. 4, pp. 102–106.*

Clark, T. R., et al, "Methylosinus trichospirium OB3b whole–cell methane momooxygenase activity in a biphasic matrix," *Applied Microbiology Biotechnology*, (1996) 45:658–663.

Soni, B. K., et al, "Technical and Economical Evaluation of Different Reactors for Methoanotrophic Cultures for Propylene Oxide Production," *Applied Biochemistry and Biotechnology*, (1998) vol. 74 pp. 115–123.

* cited by examiner

*Primary Examiner*—Irene Marx
*Assistant Examiner*—Vera Afremova
(74) *Attorney, Agent, or Firm*—Clayton Howarth & Cannon

(57) ABSTRACT

A method for microbial production of epoxides and other oxygenated products is disclosed. The method uses a biocatalyst of methanotrophic bacteria cultured in a biphasic medium containing a major amount of a non-aqueous polar solvent. Regeneration of reducing equivalents is carried out by using endogenous hydrogenase activity together with supplied hydrogen gas. This method is especially effective with gaseous substrates and cofactors that result in liquid products.

9 Claims, 4 Drawing Sheets

MICROBIAL PRODUCTION OF EPOXIDES

CONTRACTUAL ORIGIN OF THE INVENTION

This invention was made with U.S. Government support under Contract No. DE-AC07-94ID13223, now Contract No. DE-AC07-99ID13727 awarded by the U.S. Department of Energy. The U.S. Government has certain rights in the invention.

BACKGROUND OF THE INVENTION

This invention relates to microbial production of chemicals. More particularly, the invention relates to methods for microbial production of epoxides and hydroxylated chemical feedstocks in a multiphase reactor using gaseous inputs as precursors and for regeneration of reducing equivalents.

Methane monooxygenase (EC 1.14.13.25) is a multicomponent enzyme, produced by methanotrophic bacteria, which catalyzes the incorporation of atmospheric oxygen into methane to form methanol. This is the first in a series of reactions that ultimately provide energy and carbon to the cell. Methanol dehydrogenase further oxidizes methanol to form formaldehyde. Although reducing equivalents are consumed initially by the monooxygenase, the methanotrophic bacteria regenerate NADH by subsequent oxidations mediated by formaldehyde and formate dehydrogenases, respectively, the terminal product being $CO_2$ (for an excellent review, see J. D. Lipscomb, Biochemistry of the Soluble Methane Monooxygenase, 48 Annu. Rev. Microbiol. 371–399 (1994)).

Studies of methane monooxygenase refer to both a soluble (sMMO) and membrane-bound or particulate (pMMO) enzyme. The prevalent form in type II methanotrophs, such as *Methylosinus trichosporium* OB3b, and type X methanotrophs, such as *Methyloccus capsulatus*, is regulated in some fashion by the concentration of copper in the growth medium. K. J. Burrows et al., Substrate Specificities of the Soluble and Particulate Methane Monooxygenases of *Methylosinus trichosporium* OB3b, 130 J. Gen Microbiol. 3327–3333 (1984); S. H. Stanley et al., Copper Stress Underlies the Fundamental Change in Intracellular Location of Methane Monooxygenase in Methane-oxidizing Microorganisms: Studies in Batch and Continuous Culture, 5 Biotechnol. Lett. 487–492 (1983). Type I methanotrophs such as *Methylomonas methanica* typically express only pMMO, although one recent isolate has been found to be an exception to that generalization. S. -C. Koh et al., Soluble Methane Monooxygenase Production and Trichloroethylene Degradation by a Type I Methanotroph, *Methylomonas methanica* 68–1, 59 Appl. Environ. Microbiol. 960–967 (1993).

Components of sMMO from *Methylosinus trichosporium* OB3b that retained a high specific activity were initially purified by B. G. Fox et al., Methane Monooxygenase from *Methylosinus trichosporium* OB3b. Purification and Properties of a Three-component System with High Specific Activity from a Type II Methanotroph, 264 J. Biol. Chem. 10023–10033 (1989). The enzyme comprises a 245 kDa hydroxylase containing a hydroxo-bridged dinuclear iron cluster at the active site of methane oxidation, a 15.8-kDa component B, and a 38.4-kDa iron-sulfur reductase with a flavin prosthetic group.

Although not supporting growth, sMMO and pMMO will, in addition to methane, adventitiously oxidize a variety of alkanes and alkenes. C. T. Hou et al., Microbial Oxidation of Gaseous Hydrocarbons: Epoxidation of $C_2$ to $C_4$ n-alkenes by Methylotrophic Bacteria, 38 Appl. Environ. Microbiol. 127–134 (1979); D. I. Stirling et al., A Comparison of the Substrate and Electron-donor Specificities of the Methane Monooxygenases from Three Strains of Methane-oxidizing Bacteria, 177 J. Biochem. 361–364 (1979); H. Dalton, Oxidation of Hydrocarbons by Methane Monooxygenases from a Variety of Microbes, 26 Adv. Appl. Microbiol. 71–87 (1980). The substrate range of sMMO, however, also includes aromatic and alicyclic compounds, K. J. Burrows et al., supra; J. Colby et al., The Soluble Methane Monooxygenase of *Methylococcus capsulatus* (Bath). Its Ability to Oxygenate n-Alkanes, n-Alkenes, Ethers, and Alicyclic, Aromatic, and Heterocyclic Compounds, 165 J. Biochem. 395–402 (1977), ethers and heterocyclic compounds, J. Colby et al., supra, and halogenated aromatics and alkenes, J. Green & H. Dalton, Substrate Specificity of Soluble Methane Monooxygenase. Mechanistic Implications. 264 J. Biol. Chem. 17698–17703 (1989).

Currently, there is considerable interest in enzyme function in non-aqueous solvents (for reviews, see J. S. Dordick, Enzymatic Catalysis in Monophasic Organic Solvents, 11 Enzyme Microb. Technol. 194–211 (1989); P. Nickolova & O. P. Ward, Whole Cell Biocatalysis in Nonconventional Media, 12 J. Ind. Microbiol. 76–86 (1993); G. J. Salter & D. B. Kell, Solvent Selection for Whole Cell Biotransformations in Organic Media, 15 Crit. Rev. Biotechnol. 139–177 (1995)). Several beneficial and unexpected modifications of typical enzyme behavior were noted in such systems. These include enhanced enzyme activity, R. Batra & M. N. Gupta, Enhancement of Enzyme Activity in Aqueous-organic Solvent Mixtures, 16 Biotechnol. Lett. 1059–1064 (1994), increased thermostability, and alterations in substrate specificity, A. Zaks & A. M. Klibanov, Enzymatic Catalysis in Organic Media at 100° C., 224 Science 1249–1251 (1984).

Recent efforts have concentrated on applications that may be less amenable to strictly aqueous approaches, since the substrates are largely insoluble in water. Examples of such an approach include degradation of sparingly soluble xenobiotics, M. Ascon-Cabrera & J. -M. Lebeault, Selection of Xenobiotic-degrading Microorganisms in a Biphasic Aqueous-organic System, 59 Appl. Environ. Microbiol. 1717–1724 (1993), petroleum fuel desulfurization, W. R. Finnerty, Organic Sulfur Biodesulfurization in Non-aqueous Media, 72 Fuel 1631–1634 (1993), and coal modification or solubilization, E. S. Olson et al., Non-aqueous Enzymatic Solubilization of Coal-derived Materials, 72 Fuel 1687–1693 (1993); C. D. Scott et al., The Chemical Modification of Enzymes to Enhance Solubilization in Organic Solvents for Interaction with Coal, 72 Fuel 1695–1700 (1993).

Production of propylene oxide from propylene for use as a chemical feedstock has been investigated using immobilized whole cells. L. E. S. Brink & J. Tramper, Production of Propene Oxide in an Organic Liquid-phase Immobilized Cell Reactor, 9 Enzyme Microb. Technol. 612–618 (1987); C. T. Hou, Propylene Oxide Production from Propylene by Immobilized Whole Cells of Methylosinus sp. CRL-31 in a Gas-solid Bioreactor, 19 Appl. Microbiol. Biotechnol. 1–4 (1984).

T. R. Clark & F. F. Roberto, *Methylosinus trichosporium* OB3b Whole-cell Methane Monooxygenase Activity in a Biphasic Matrix, 45 Appl. Microbiol. Biotechnol. 658–663 (1996), demonstrated soluble methane monooxygenase activity in a two-phase (biphasic) matrix comprising a buffered aqueous phase and 2,2,4-trimethylpentane (isooctane) using reconstituted whole-cell preparations of lyophilized *Methylosinus trichosporium* OB3b. The rate of conversion of gaseous propylene to propylene oxide, a non-metabolized liquid, was used as the primary measure of enzymatic activity. Appreciable soluble methane monooxygenase activity was detected when the volume of the aqueous phase represented at least 1% of the total volume, although the initial rate of product formation did increase as the volume of the aqueous phase increased. In comparison to the aqueous system, the specific rate and yields in the biphasic system were much less sensitive to increases in the concentrations of formate and protein (i.e., the methane monooxygenase). There was some evidence, however, that the enzyme system was more stable in the biphasic matrix, since the rate of propylene oxide formation remained linear for an extended period of time. $V_{(app.)}$ in the biphasic system decreased by a factor of 0.6 relative to the same parameter in the aqueous system. Conversely, $K_{m(app.)}$ for propylene was 1.6 times greater in the biphasic system. Hence, the apparent catalytic efficiency in the aqueous system was four times that in the biphasic system, as indicated by a decrease in the corresponding ratios of $V_{(app.)}$ to $K_{m(app.)}$.

In view of the foregoing, it will be appreciated that providing a method for microbial production of epoxides and hydroxylated hydrocarbons would be a significant advancement in the art.

BRIEF SUMMARY OF THE INVENTION

It is an object of the present invention to provide a method for microbial production of epoxides and hydroxylated hydrocarbons in a continuous production format.

It is also an object of the invention to provide a method for microbial production of epoxides and hydroxylated hydrocarbons that utilizes gaseous inputs and produces liquid products.

It is another object of the invention to provide a method for microbial production of epoxides and hydroxylated hydrocarbons that results in regeneration of reducing equivalents.

It is still another object of the invention to provide a method for microbial production of epoxides and hydroxylated hydrocarbons that uses a liquid phase comprising (i) a non-polar, non-aqueous solvent or mixture of miscible non-polar, non-aqueous solvents and (ii) an aqueous phase.

It is yet another object of the invention to provide a method for microbial production of epoxides and hydroxylated hydrocarbons wherein a hydrated biocatalyst can be immobilized on a non-porous support material and submerged in the non-polar, non-aqueous solvent phase.

It is a further object of the invention to provide a method for microbial production of epoxides and hydroxylated hydrocarbons wherein non-aqueous solvents have low vapor pressures, much higher boiling points than reaction products, and are non-inhibitory to methane oxidizing microorganisms.

It is a still further object of the invention to provide a method for microbial production of epoxides and hydroxylated hydrocarbons wherein water and other polar molecules, such as reaction products, are insoluble in the non-aqueous solvents.

It is another object of the invention to provide a method for microbial production of epoxides and hydroxylated hydrocarbons wherein the gaseous substrates are readily soluble in the non-aqueous solvents.

It is still another object of the invention to provide a method for microbial production of epoxides and hydroxylated hydrocarbons wherein the products are polar and readily soluble in the aqueous phase.

It is yet another object of the invention to provide a method for microbial production of epoxides and hydroxylated hydrocarbons wherein the density of the non-aqueous phase is much greater than the density of the aqueous phase such that a stable, self-maintaining phase separation is obtained.

These and other objects can be addressed by providing a method for microbial production of an oxygenated derivative of a methane-monooxygenase substrate comprising:

(a) incubating a reconstituted lyophilized whole cell enzyme preparation of methanotrophic bacteria containing methane monooxygenase and hydrogenase in a bioreactor, said bioreactor comprising a biphasic liquid phase comprising a major amount of a non-polar non-aqueous solvent and a minor amount of a polar aqueous medium, a non-aqueous solvent circulation circuit for circulating said non-polar non-aqueous solvent through the bioreactor, and an aqueous medium circulation circuit for circulating the polar aqueous medium through the bioreactor in a counter-current manner as compared to the non-polar non-aqueous solvent;

(b) continuously dissolving effective amounts of oxygen gas, hydrogen gas, and a gaseous substrate in the non-polar non-aqueous solvent, wherein the gaseous substrate is readily soluble in the non-polar non-aqueous solvent and is susceptible to oxidation by the methane monooxygenase to result in the oxygenated derivative thereof, wherein the oxygenated derivative is a polar liquid;

(c) circulating the non-polar non-aqueous solvent in close proximity to the reconstituted lyophilized whole cell enzyme preparation of methanotrophic bacteria containing methane monooxygenase and hydrogenase such that the methane monooxygenase oxidizes the gaseous substrate into the oxygenated substrate;

(d) circulating the polar aqueous medium in a counter-current manner through the circulating non-polar non-aqueous solvent such that the oxygenated substrate is partitioned into the polar aqueous medium; and (e) removing and recovering the oxygenated substrate from the polar aqueous medium and recycling the non-polar non-aqueous solvent and the polar aqueous medium.

Many substrates and products can be used in this method, but a preferred substrate is propylene, and the resulting preferred oxygenated derivative is propylene oxide. Preferred methanotrophic bacteria according to the invention are selected from the group consisting of Methylosinus, Methyloccus, and Methylomonas, and mixtures thereof. Especially preferred methanotrophic bacteria are *Methylosinus trichosporium* OB3b. Preferred non-polar non-aqueous solvents according to the invention are isooctane, hexane, silicone oil, hexadecane, fluorocarbons, and mixtures thereof.

Another preferred embodiment of the invention comprises a method for regenerating reducing equivalents in a bioreactor configured for utilizing reducing equivalents in a methane-monooxygenase-catalyzed reaction for oxidizing a substrate into an oxygenated product comprising:

(a) incubating a reconstituted lyophilized whole cell enzyme preparation of methanotrophic bacteria containing methane monooxygenase and hydrogenase in the bioreactor, the bioreactor comprising a liquid phase comprising a major amount of a non-polar non-aqueous solvent and a minor amount of a polar aqueous medium; and (b) continuously dissolving an effective amount of hydrogen gas in the non-polar non-aqueous solvent, such that the hydrogen gas and $NAD^+$ are converted by the hydrogenase into NADH, thereby regenerating reducing equivalents.

Still another preferred embodiment of the invention comprises a method for preparing a lyophilized preparation of methanotrophic bacteria for use as a biocatalyst comprising:

(a) culturing the methanotrophic bacteria, concentrating the resulting cells, resuspending the concentrated cells, and then chilling the resuspended cells at about 0° C.;

(b) freezing the chilled cells at about −50° C. using a shell freezer;

(c) further cooling the frozen cells in a liquid nitrogen bath and then freeze drying the resulting cells using a lyophilizer for a period sufficient to obtain a powdered cell preparation; and (d) storing the powdered cell preparation under refrigeration.

A still further preferred embodiment of the invention comprises a method for propagating methanotrophic bacteria comprising culturing the bacteria in a liquid medium comprising a major amount of a non-aqueous polar solvent and a minor amount of a known methanotrophic bacterial growth medium.

DETAILED DESCRIPTION

Before the present methods for microbial production of epoxides and hydroxylated chemicals are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "oxygenated derivative of a methane-monooxygenase substrate" means an oxidation product of a methane-monooxygenase-catalyzed reaction. For example, propylene oxide is an oxygenated derivative of propylene.

As used herein, "methanotrophic bacteria" means bacteria that produce methane monooxygenase, such as *Methylosinus trichosporium* OB3b, *Methyloccus capsulatus*, and *Methylomonas methanica.*

As used herein, "major amount" means greater than 50%, and "minor amount" means less than 50%.

Figure 1:
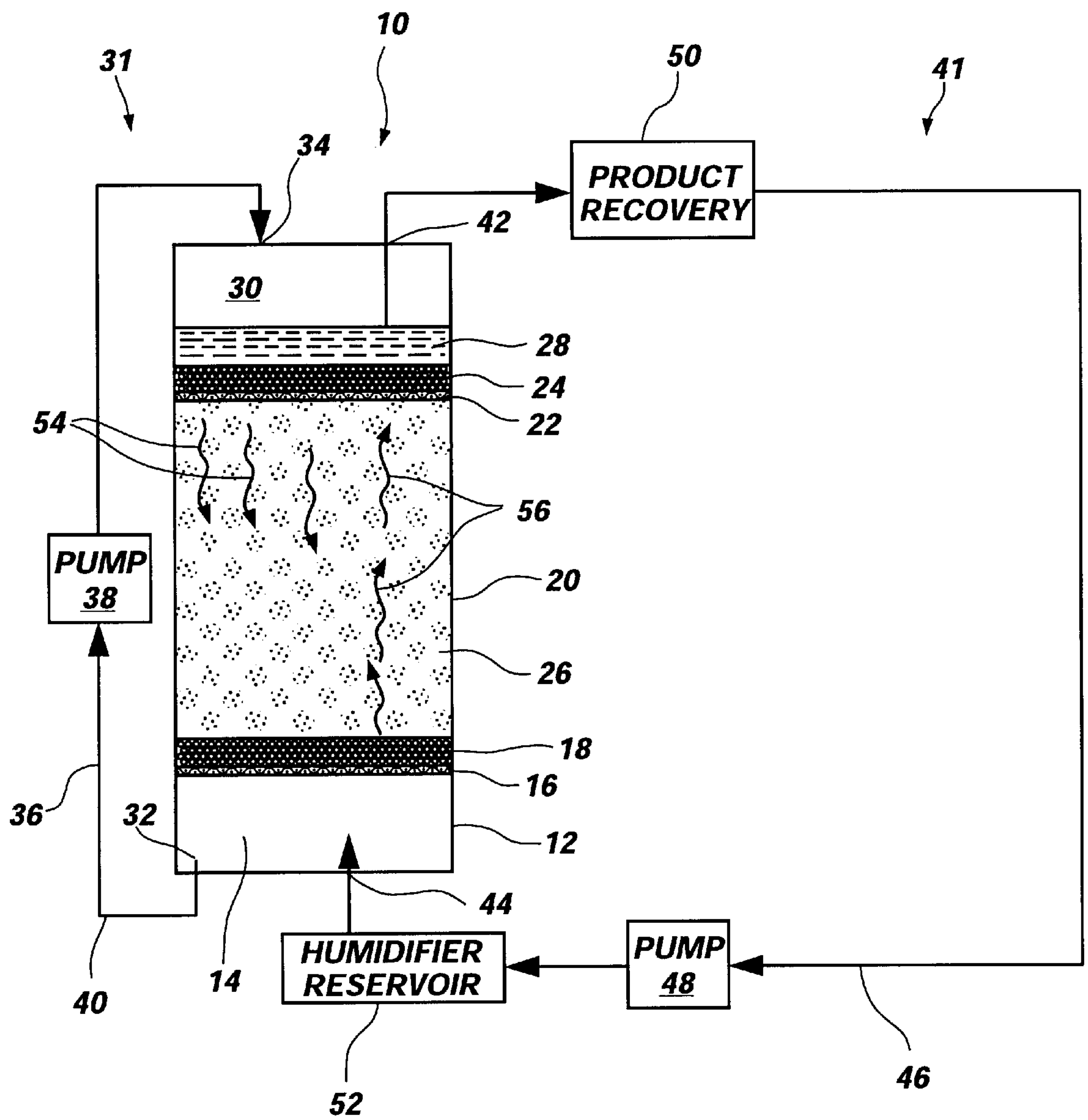
FIG. 1 shows a schematic diagram of a bioreactor for use in microbial production of epoxides and hydroxylated chemicals according to the present invention.

FIG. 1 shows an illustrative bioreactor suitable for use according to the present invention. The bioreactor 10 comprises a housing 12, preferably constructed of glass or another material that is non-porous and unreactive to the contents of the bioreactor. The housing 12 defines a chamber 14 for receiving the contents of the bioreactor, which will be described below. At a lower level in the chamber there is suspended a lower bead support 16, which is a porous layer that permits the passage of liquids and gases, but retains glass beads and similar particles. Disposed on the lower bead support is a layer of glass beads 18 or similar material, which serves the functions of a diffuser layer and phase separator. A layer comprising the immobilized biocatalyst 20 is disposed on the layer of glass beads. The biocatalyst is a reconstituted whole-cell preparation of lyophilized methanotrophic bacteria, such as *Methylosinus trichosporium* OB3b. This biocatalyst will be described in more detail below. Disposed above the biocatalyst layer is an upper bead support 22, which can be the same material as the lower bead support described above. Disposed on the upper bead support is another layer of glass beads 24, which functions as another diffuser layer. The chamber is partially filled with a non-polar, non-aqueous solvent or mixture of miscible non-polar, non-aqueous solvents that forms a non-aqueous solvent layer 26, and disposed above the non-aqueous solvent layer is an aqueous layer 28. There should be a headspace 30 above the aqueous layer, which is not occupied with a liquid layer.

The bioreactor further comprises a non-aqueous solvent circulation circuit 31 for circulating the non-aqueous solvent and gases dissolved therein through the bioreactor and for injecting gases into the bioreactor. This circuit comprises a non-aqueous solvent exit port 32 disposed at a lower level of the housing and preferably at a level below the lower bead support such that glass beads, immobilized catalyst, and the like do not have access to the non-aqueous solvent exit port. A non-aqueous solvent entrance port 34 is also disposed in the housing, but at a level above the aqueous layer, i.e., in the portion of the housing adjacent to the headspace. Coupled to the non-aqueous solvent exit port and the non-aqueous solvent entrance port is a tube 36 having an in-line pump 38 for pumping the non-aqueous solvent from the non-aqueous solvent exit port to the non-aqueous solvent entrance port, thus circulating the non-aqueous solvent through the bioreactor. A gas injection port 40 is also disposed in the tube, through which gases, such as oxygen, hydrogen, methane, propylene, and the like, can be injected into the bioreactor. The gases are completely soluble in the non-aqueous solvent, thus the gases are circulated through the bioreactor by being dissolved in the non-aqueous solvent.

The bioreactor further comprises an aqueous solvent circulation circuit 41 for circulating the aqueous solvent through the bioreactor and for recovering the product from the aqueous solvent. An aqueous solvent exit port 42 is disposed in the housing adjacent to the aqueous layer such that the aqueous solvent can exit the chamber and be circulated through the aqueous solvent circulation circuit. An aqueous solvent entrance port 44 is disposed in the housing at a lower level thereof, preferably below the level of the lower bead support. A tube 46 is disposed on both the aqueous solvent exit port and the aqueous solvent entrance port for connecting these two ports, and an in-line pump 48 is disposed on the tube for pumping the aqueous solvent from the aqueous solvent exit port to the aqueous solvent entrance port. Also coupled to the tube is a product recovery member 50 for removing the product from the aqueous solvent and recovering the product. Still further, a reservoir 52 is also preferably present in the aqueous solvent circulation circuit for holding an amount of aqueous solvent, which can be directed back into the chamber by the action of the pump.

In operation, the bioreactor functions as follows. The non-aqueous solvent circulation circuit removes non-aqueous solvent from the chamber, injects substrate gases in preselected amounts into the non-aqueous solvent, and returns the non-aqueous solvent, now containing the dissolved gases, to the chamber at the top of the packed column. The flow rate can be much less than in a corresponding aqueous system because the relative concentrations of substrates are, in some cases, orders of magnitude higher than could be achieved in water. Because of the immiscibility of water in the non-aqueous solvent and the density differences between these phases, a distinct aqueous layer 28 forms above the non-aqueous layer 26. As the non-aqueous solvent passes through the layer containing the catalyst, the substrate gases, i.e., oxygen, hydrogen, and, for example, methane, come in close proximity with the catalyst, which oxidizes the methane into methanol, a polar product, by the action of methane monooxygenase. The methanol product tends to partition out of the non-aqueous solvent and into the much more polar aqueous phase. The hydrogen gas is used in regenerating reducing equivalents by the hydrogenase-catalyzed reaction that results in the conversion of $NAD^+$ into NADH. As described above, the oxygen and methane are used in oxidizing the methane to methanol. Thus, if there were no replenishment of these gases, the non-s aqueous solvent would become depleted with respect to the substrate gases. An aqueous phase introduced into the chamber at the bottom of the packed column tends to collect or "sweep up" any polar product as the aqueous solvent moves up through the column because of the relative densities of the phases. Therefore, product recovery can be achieved by collecting the aqueous phase representing only a small percentage of the total reactor volume. The aqueous phase is recycled following product recovery. Since the mixed organic phase is also recycled, neither liquid phase requires replacement, thus reducing both material and waste disposal costs. It should be further noted that the non-aqueous phase tends to circulate from top to bottom of the bioreactor, as indicated by arrows 54. At the same time, the aqueous phase tends to circulate from bottom to top of the bioreactor, as indicated by arrows 56. Thus, the counter-current circulation of the non-aqueous phase and the aqueous phase works to increase the efficiency of partition of the polar reactions product into the aqueous phase.

EXAMPLE 1

Materials and Methods

Culture maintenance. *M trichosporium* OB3b (ATCC 35070) was maintained at 30° C. in serum vials containing Higgins minimal nitrate salts medium (NSM) amended with 2 $\mu$M Cu and, as recommended by S. Park et al., Batch Cultivation of *Methylosinus trichosporium OB*3b. 1. Production of Soluble Methane Monooxygenase, 38 Biotechnol. Bioeng. 423–433 (1991), 80 $\mu$M Fe(II). The headspace composition was adjusted to a 70:30 v/v mixture of air and methane. The vials were shaken at a rate of 200–225 rpm. Alternatively, the culture was maintained on Fe- and Cu-amended NSM medium solidified with 1% w/v agarose (Sigma type 1-A). The plates were incubated at 30° C. in a vacuum desiccator containing an atmosphere of 70% v/v air and 30% v/v methane.

Continuous-flow cultures. A 1-liter bioreactor (Bellco) containing 550–600 ml NSM medium and 80 $\mu$M Fe(II) was inoculated with cells from the batch culture (8% v/v). The reactor contents were stirred with an $N_2$-driven magnetic impeller and sparged with an air:methane mix (70:30 v/v), although initial growth lags were reduced by sparging with 2% V/V $CO_2$ in addition to air and methane until log-phase growth commenced. S. Park et al., supra. The reactor was maintained in a continuous flow mode (dilution rate, D=0.02 $h^{-1}$) using a cartridge-type peristaltic pump (Masterflex). Temperature was monitored using a type YM thermistor and maintained at 30° C. by a temperature controller (Digi-Sense, Cole Parmer), input controller (Type 45500, Thermolyne) and heat tape.

Lyophilization. The bioreactor was switched to batch mode approximately 24 hours prior to cell harvest to allow the cells to reach late log or stationary phase, as determined by comparison of absorbance (600 nm) to a growth curve. The cells were harvested and immediately centrifuged at 12,000 g (Sorvall RC5b, SS-34 rotor) for 10 minutes at 4° C. The pellets were washed once at pH 7.0 with one of two MOPS [3-(N-morpholino)propanesulfonic acid] buffers: MOPS/Mg was comprised of 25 mM MOPS and 5 mM $MgSO_4$; MOPS/Cys/Fe was comprised of 25 mM MOPS, 2 mM cysteine, and 0.2 mM $Fe(NH_4)_2(SO_4)_2 \cdot 6H_2O$. B. G. Fox et al., supra; D. R. Jollie & J. D. Lipscomb, Formate Dehydrogenase from *Methylosinus trichosporium* OB3b, 188 Methods Enzymol. 331–334 (1990). The presence of sMMO was verified by qualitative assays for both propylene and naphthalene oxidation. G. A. Brusseau et al., Optimization of Trichloroethylene Oxidation by Methanotrophs and the Use of Colorimetric Assay to Detect Methane Mono-oxygenase Activity, 1 Biodegradation 19–29 (1990). The cells were resuspended in a minimal volume of this same buffer containing 10 mM NADH (Kodak), which was found to have cryoprotective properties, frozen at −75° C for 1 hour or by immersion in liquid nitrogen, and lyophilized.

Protein assay. Lyophilized cells were resuspended in 0.1 M NaOH to concentrations between 0.05% and 0.1% w/v. The samples were heated for 5 minutes in Eppendorf tubes submerged in a boiling water bath. Samples comprising 50 μl cell digest were added to 2.5 ml of BioRad protein reagent (diluted 1:4) and the absorbance (595 nm) was read immediately using a Shimadzu UV-1201 spectrophotometer. Absorbance values were quantified by comparison to a standard regression curve using bovine serum albumin as a standard.

Naphthalene oxidation assay. The production of sMMO was verified by demonstrating the capability of washed cells to hydroxylate naphthalene, with a positive reaction for sMMO determined by a color reaction upon the addition of tetrazotized o-dianisidine dye. G. A. Brusseau et al., supra.

Propylene oxidation assay. Lyophilized cell preparations were assayed for MMO activity, which is defined herein as the quantity of propylene oxide formed per milligram of protein (total) per hour. The reaction vessels consisted of vials with 10 ml headspace sealed with aluminum caps and polytetrafluoroethylene-lined butyl rubber septa. Lyophilized cells were rehydrated to various degrees with buffer for aqueous and biphasic activity assays. Sodium formate (Alfa) was then added to the rehydrated cell suspensions for the purpose of regenerating NADH. Isooctane (Fisher) was added to the appropriate reaction vials. Assuming a total liquid-phase volume of 1000 μl, the final formate concentrations for the aqueous and biphasic systems were, respectively, 1360 μM and 13.6 μM, unless otherwise stated. The reaction mixtures were warmed to 28° C., unless otherwise stated, prior to the addition of substrate. Following injection of propylene into the headspace (89 μmol, aqueous; 44.6 μmol, biphasic), the vials were shaken at 150 rpm or 200 rpm on a rotary shaker (New Brunswick G-24). The reaction was stopped by the addition of methanol (74 mM or 124 mM), which was found to inhibit the reaction completely in the biphasic system and by approximately 99% in assays using an aqueous matrix. The entire contents of the reaction vials were sacrificed for each analysis.

Gas chromatography. Propylene oxide formation was quantified with a Shimadzu model GC-14A gas chromatograph containing a glass column (2.6 mm inner diameter, 3.1 m) packed with 80×100 mesh Carbopack C+0.1% SP-1000 (Supelco). The gas chromatograph was configured with an AOC-17 auto-injector and a Shimadzu CR-601 Chromatopac recorder. Helium was used as a carrier gas (20 ml/min). The injector and detector (flame-ionization detector) temperatures were respectively 200° C. and 175° C. Aqueous samples were run isothermally at 80° C. for 6 minutes. Isooctane samples were determined as follows: 80° C. for 2 minutes; ramped at 40° C./minute to a final temperature of 200° C.; and held for 6 minutes at 200° C. Product formation was quantified in the single-time-point assay by comparison of peak area to a standard regression curve.

Propylene available in solution was determined separately under the same conditions listed above, but in the presence of the lyophilized cell preparation. The extent of product partitioning was examined by separating the isooctane phase from the hydrated cells, normalizing the volumes, and determining the product concentration.

Kinetic parameters. Since the range of liquid-phase substrate concentrations was narrow in both matrices, despite the headspace concentration, fitted plots of substrate versus velocity were used in favor of approaches involving reciprocal plots. $V_{(app.)}$ and $K_{m(app.)}$ were estimated by computer-fitting a second-order polynomial expansion to plots of propylene concentration against the rate of product formation (nmol propylene oxide $mg^{-1}$ protein $h^{-1}$).

Results

Propylene and propylene oxide partitioning. Propylene rapidly partitioned between the headspace and liquid phase in both the aqueous and biphasic systems. The presence of lyophilized cells and associated buffer salts did not affect the concentration of propylene ([S]) in the liquid phase. The maximum solution concentrations for the aqueous and biphasic matrices were respectively 8.5 μM and 26.7 μM. The concentration of propylene in solution remained constant during the course of incubation because of a large excess present in the headspace.

Propylene oxide was not detected in normalized fractions containing the hydrated cells. This indicated that measurement of propylene oxide concentrations in the water-saturated isooctane phase provided an accurate estimate of total product formation.

Figure 2:
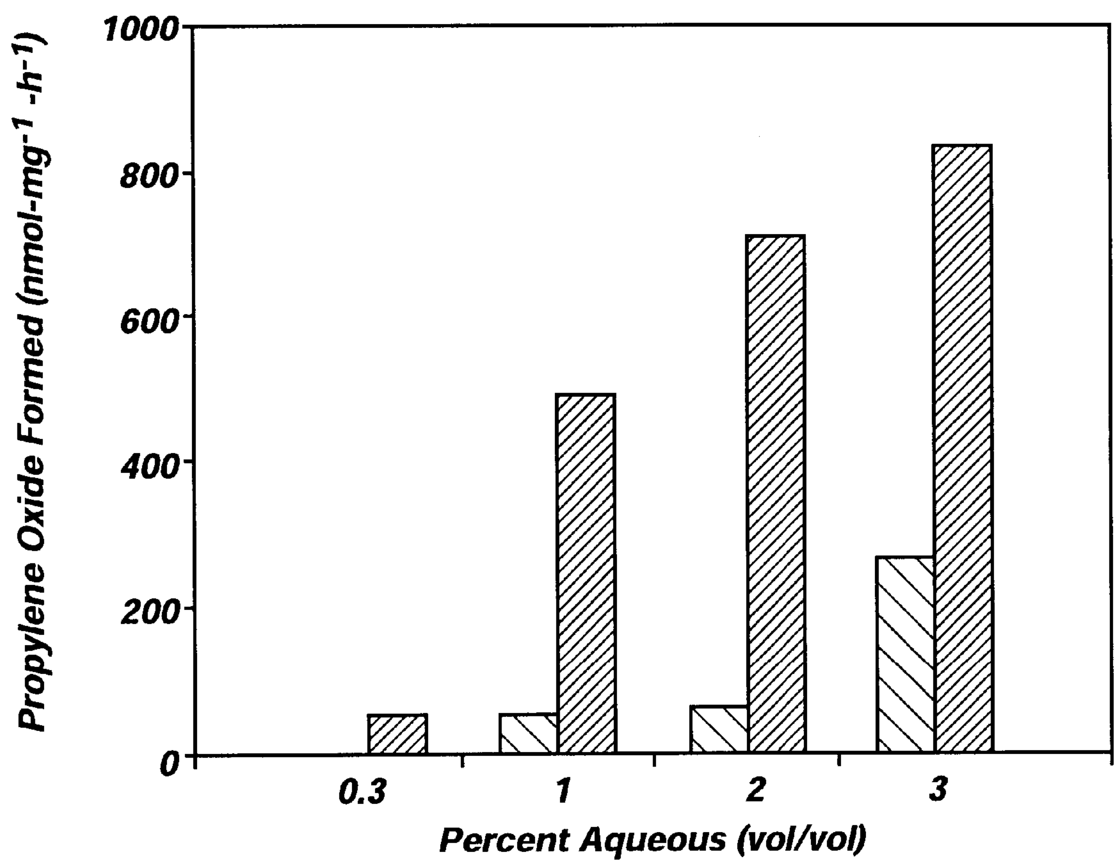
FIG. 2 shows the effect of the aqueous-phase concentration on the specific rate of propylene epoxidation by lyophilized whole cells of *M trichosporium* OB3b in a biphasic matrix. Rates were determined without the addition of exogenous formate (hatched bars) and with 40.8 μM formate (solid bars). The matrix (1000 μl) was composed of isooctane + indicated percentages of MOPS/Cys/Fe buffer (pH 7.0)+190 μg protein. Incubation was at 150 rpm at 21° C.

Aqueous phase concentration. Rehydration of the cellular biocatalyst was a requirement for attaining appreciable rates of formation of propylene oxide. As shown in FIG. 2, the formate-stimulated rate increased ninefold when the aqueous-phase concentration in the biphasic matrix was increased from 0.3% to 1.0% v/v. Propylene epoxidation in the absence of formate represented a maximum of 11% of the total activity in the biphasic system until the aqueous-phase content increased to 3% v/v, when a marked increase in endogenous activity was noted. In this case, however, the increase in endogenous activity did not result in a proportional increase in the overall rate.

Figure 3:
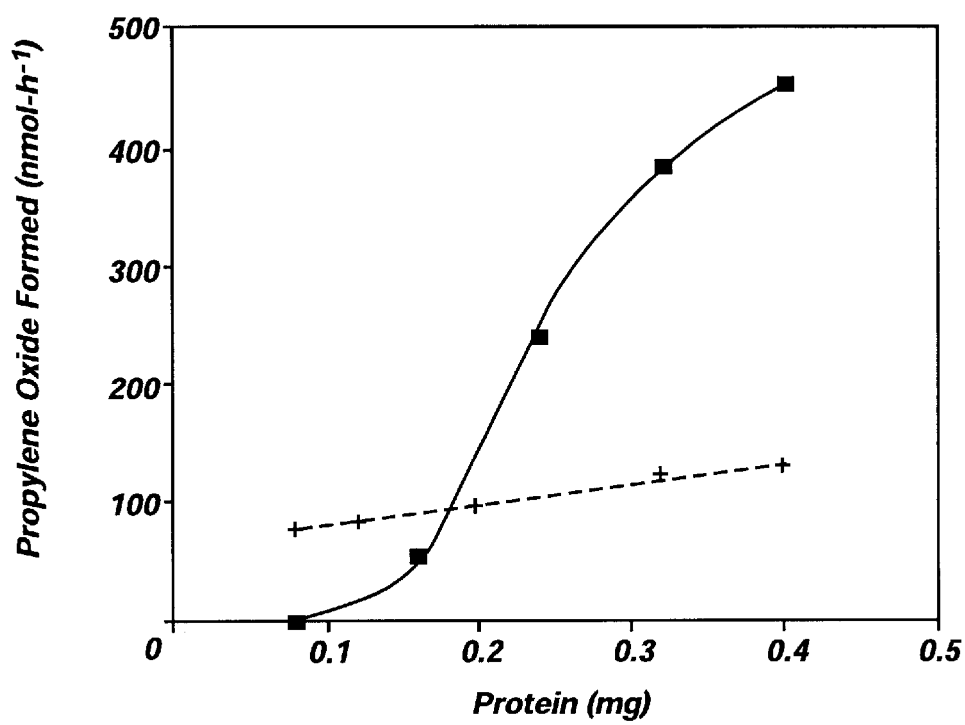
FIG. 3 shows the effect of protein concentration on the rate (nmol $h^{-1}$) of propylene oxide formation in 1000 μl aqueous and biphasic matrices composed of respectively MOPS/Mg buffer containing 1020 μM formate (■) or 98% v/v isooctane +2% v/v MOPS/Mg containing 13.6 μM formate (+). Protein amounts were 80–400 μg, and incubation was at 200 rpm at 28° C.

Protein concentration. The aqueous and biphasic matrices differed with respect to an optimum enzyme concentration. FIG. 3 compares the effect of total protein, hence the concentration of sMMO, on the rate of propylene oxide accumulation (nmol $h^{-1}$) in both matrices. Note that an increase in protein concentration in the biphasic system resulted in a linear increase in the rate, while a sigmoidal response was noted for the aqueous matrix with respect to this same parameter. Clearly, the biphasic system was much less responsive to increases in enzyme concentration. Therefore, unlike the aqueous system, the specific activity (nmol $mg^{-1}$ protein $h^{-1}$) in the biphasic system also declined steadily with increasing concentrations of protein, with the greatest rate attained at the lowest protein concentration examined. There was also a considerable difference in the overall rates (nmol $h^{-1}$) for the two systems.

Figure 4:
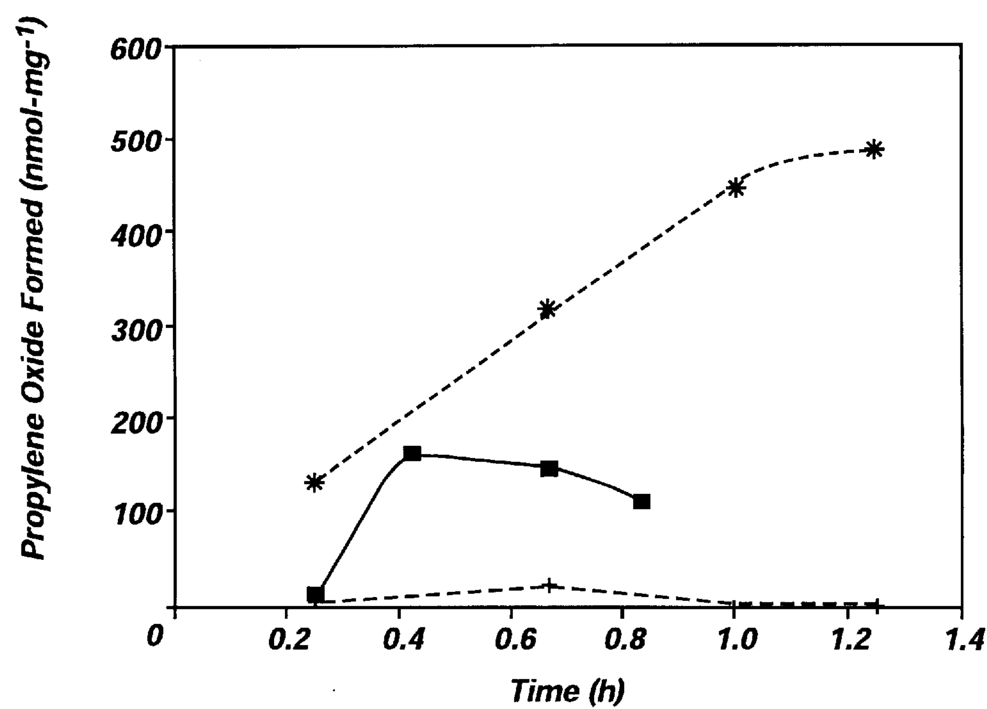
FIG. 4 shows yields of propylene oxide (nmol $mg^{-1}$ protein) in 1000 μl aqueous and biphasic matrices containing low concentrations of protein. Matrices contained 80 μg protein and were composed of MOPS/Mg buffer or 98% v/v isooctane+2% v/v MOPS/Mg buffer: Biphasic +13.6 μM formate (*); aqueous+13.6 μM formate (+); aqueous+1020 μM formate (■). Incubation was at 200 rpm at 28° C.

Formate concentration. The extent to which formate stimulated activity in the aqueous system depended on the protein concentration. At the high end of the concentration range, specific rates of product formation increased as the formate concentration was increased to 1320 μM. At low concentrations of protein, however, activity in the aqueous system never exceeded biphasic activity. As shown in FIG. 4, the yield in the aqueous system was less than that of the biphasic system whether low (13.6 μM) or high (1020 μM) formate concentrations were used.

In contrast to the aqueous system, activity in the biphasic system was generally unresponsive to additions of formate in excess of 13.6 μM. In fact, the maximum formate concentration in the aqueous system (1360 μM) was somewhat inhibitory in the biphasic system and decreased the rate in one experiment by 21% (data not shown).

Enzyme stability. There was evidence that sMMO and/or formate dehydrogenase may have been stabilized (i.e., a greater number of turnovers per unit time) in the biphasic matrix. FIG. 4 also summarizes yields (nmol mg-l protein) in aqueous and biphasic matrices containing a low concentration of protein. Negligible aqueous activity resulted at low protein (80 μg/ml) and formate (13.6 μM) concentrations. An increase in yield did result from increasing formate availability (1020 μM), indicating that the conversion of substrate to product with only 13.6 μM formate was formate (NADH)-limited. However, product also ceased to accumulate after 25 minutes at the much higher formate concentration although yield was less than when using higher concentrations of protein. In a separate experiment, the rate of product formation under optimum conditions for the aqueous matrix (high concentrations of both protein and formate) decreased by 46% over a 0.5-hour incubation period. Therefore, substantial loss of sMMO activity was experienced under aqueous conditions within 30 minutes regardless of the enzyme concentration and amount of formate provided as reductant.

Conversely, the yield in the biphasic system was proportional to incubation time for a period of 60 minutes. Despite greater yields than in the aqueous system, the specific activity was also relatively constant during this period, demonstrating that neither substrate depletion (propylene, $O_2$, NADH) nor product inhibition was responsible for the 0 differences in yield.

Kinetic parameters. The data in Table 1 represent typical values for the biphasic and aqueous whole-cell sMMO activity. Greater bulk-phase substrate concentrations in the biphasic system were somewhat offset by a higher $K_{m(app.)}$ than was determined for the aqueous system. The apparent catalytic efficiency was four times greater in the aqueous system than for the same preparation in the biphasic system, as indicated by a decrease in the ratio of corresponding values of $V_{(app.)}$ to $K_{m(app.)}$ for each system.

TABLE 1

| Matrix | $V_{(app.)}$ | $K_{m(app.)}$ |
|---|---|---|
| Aqueous | 973 | 8.3 |
| Biphasic | 366 | 13.0 |

The correlation coefficients for second-order polynomial curve fits: aqueous r2=0.984; biphasic, r2=0.822. The aqueous phase consisted of MOPS/Mg buffer. The biphasic matric was comprised of 98% v/v isooctane+2% v/v MOPS/Mg buffer.

Discussion

The use of lyophilized cell preparations that catalyze multi-enzyme reactions in biphasic systems has been reported for yeast. F. Borzeix et al., Bi-enzymatic reaction for alcohol oxidation in organic media: from purified enzymes to cellular systems, 17 Enzyme Microb. Technol. 615–622 (1995). In the present study, however, the primary advantages of using lyophilized cells included ease of control of the aqueous content and generation of a stable biocatalyst that contained both sMMO and formate dehydrogenase activities, the latter being required for cofactor regeneration.

A sufficient aqueous-phase content, however, was critical for enzyme activity to occur. The system was not sufficiently dissected to determine the extent of overlap of the individual optimum aqueous-phase contents for formate dehydrogenase, sMMO, or enzymes required for the utilization of endogenous sources of reducing equivalents. A range in optima is indicated by the increase in endogenous propylene oxidation activity upon increasing the aqueous-phase content.

The rate of propylene oxide formation in the biphasic matrix declined only slightly over a period exceeding 1 hour, indicating that sMMO was not rapidly inactivated under these conditions. It was also discovered that the rate of propylene oxide formation in the biphasic system was largely unresponsive to increases in the concentration of formate in excess of an optimum concentration, which was, unexpectedly, much less than the optimum for the aqueous system. Together, these findings are at least suggestive that lability of formate dehydrogenase, D. C. Yoch et al., Formate Dehydrogenase from the Methane Oxidizer *Methylosinus trichosporium* OB3b, 172 J. Bacteriol. 4456–4463 (1990); D. R. Jollie & J. D. Lipscomb, Formate Dehydrogenase from *Methylosinus trichosporium* OB3b. Purification and spectroscopic characterization of the cofactors, 266 J. Biol. Chem. 21853–21863 (1991), and not sMMO may have been one factor that defined the overall rates of propylene oxide formation in the biphasic system. Problems associated with the use of dehydrogenases for regeneration of NADH by methanotrophs have long been recognized. C. T. Hou et al., Epoxidation of Alkenes by Methane Monooxygenase: Generation and Regeneration of Cofactor, $NADH_2$, by Dehydrogenase, 4 J. Appl. Biochem. 379–383 (1982).

It is significant that the $K_{m(app.)}$ for propylene conversion by reconstituted lyophilized cell preparations in the biphasic system, as described above, is within an order or magnitude of previously reported values for the purified enzyme. J. Green & H. Dalton, Steady-state Kinetic Analysis of Soluble Methane Monooxygenase from *Methylococcus capsulatus* (Bath), 236 J. Biochem. 155–162 (1986). This indicates that the reconstituted cells may have damaged membranes and be somewhat leaky. An increase in this kinetic parameter would not be surprising since the presence of saturating concentrations of an organic solvent (in this case, isooctane) might reduce the stability of the enzyme-substrate complex, resulting in an apparent increase in the $K_{m(app.)}$. J. S. Dordick, supra.

The wide substrate range of sMMO, J. Colby et al., supra, precluded the use of many solvents because of the potential for competitive inhibition, a problem not entirely obviated by the use of isooctane. This was indicated by the substantial decrease in the ratio of $V_{(app.)}$ to $K_{m(app.)}$ for sMMO, J. Green & H. Dalton, 236 J. Biochem. 155–162 (1986), in the biphasic system. Maintenance of this system in a biphasic matrix, however, is particularly interesting since this process involves not one, but two separate multicomponent enzymes (methane monooxygenase and formate dehydrogenase) and is most promising for processing a wide variety of organic substrates.

EXAMPLE 2

In this example the procedure of Example 1 was followed except that the bacteria used were mixed methanotrophs isolated from raw water/sediment samples from Test Area North ("TAN") injection well #1 at the Idaho National Engineering and Environmental Laboratory, Idaho Falls, Id. These bacteria were cocci or diplococci that appeared morphologically similar to *M capsulatus*. The cells were grown in a stirred bioreactor containing NSM+80 mM Fe. After concentration, the cells were resuspended and cooled in an ice/water bath. The cell suspension was added to lyophilization jars at approximately 0° C. and chilled to approximately −50° C. using a glycol shell freezer. The frozen cells were cooled further in a liquid nitrogen bath and placed on a lyophilizer for a period that usually extended overnight (40 mT, −90° C.). The resulting dry powder was manually homogenized with a spatula, divided into aliquots, placed in sealed headspace vials, and refrigerated prior to use in assays for propylene oxide formation. To prevent condensation on the lyophilized powder, the vials were allowed to warm to room temperature prior to opening and use. The lyophilized preparations were stored for six days at −73 ° C. before use. Sodium formate (Alfa) was added to the rehydrated cell suspensions for the purpose of regenerating NADH in some samples ("(+) formate"), but not in other samples ("(−) formate"). The results shown in Table 2 are based on assays performed in triplicate.

TABLE 2

| Preparation | nmol* $mg^{-1*}$ $h^{-1}$ ($X \pm s_{n-1}$) | % Washed Cell Activity |
|---|---|---|
| | Washed Whole Cells | |
| (−) formate | 2106 ± 274 | 100 |
| (+) formate | 9201 ± 228 | 100 |
| | Reconstituted Lyophilized Cells | |
| (−) formate | 179 ± 212 | 8.5 |
| (+) formate | 7959 ± 1251 | 86.5 |

As was typical with many experiments, the endogenous methane monooxygenase activity was reduced following lyophilization. The level of activity obtained with lyophilized cell preparations with formate added for regenerating reducing equivalents, was unexpectedly high.

These results show that unexpectedly and surprisingly high methane monooxygenase activity was obtained in cells lyophilized according to the present invention as compared to washed whole cells.

EXAMPLE 3

In this example the procedure of Example 1 was followed except that whole cells were used instead of lyophilized cells, the cells were cultured in aqueous medium (NSM) without Mo and Ni supplementation, the headspace gas compositions contained either ambient or about 20% ambient (low) oxygen concentrations, and sodium formate was not added to all cultures. Some cultures contained added formate, whereas other cultures contained hydrogen gas added to the headspace gas composition to assay endogenous hydrogenase activity for regenerating reducing equivalents, and other cultures contained no added formate or hydrogen, for assaying endogenous sMMO activity. The data presented in Table 3 show the rates of propylene oxide formation and represent the means values for three vials per test group.

TABLE 3

| | Rate of Propylene Oxide Formation (nmol* $mg^{-1}$ protein* $h^{-1}$ | | |
|---|---|---|---|
| Headspace | Endogenous | Formate | Hydrogen |
| Low Oxygen | 6068 ± 102 | 5476 ± 552 | 9824 ± 410 |
| Ambient Oxygen | 6583 ± 705 | 11319 ± 524 | 11156 ± 358 |

These results show that hydrogen gas can be used to regenerate reducing equivalents in whole cells cultured in aqueous medium according to the reaction:

$$NAD^+ + H_2 \xrightarrow{H_2ase} NADH + H^+.$$

EXAMPLE 4

Figure 5:
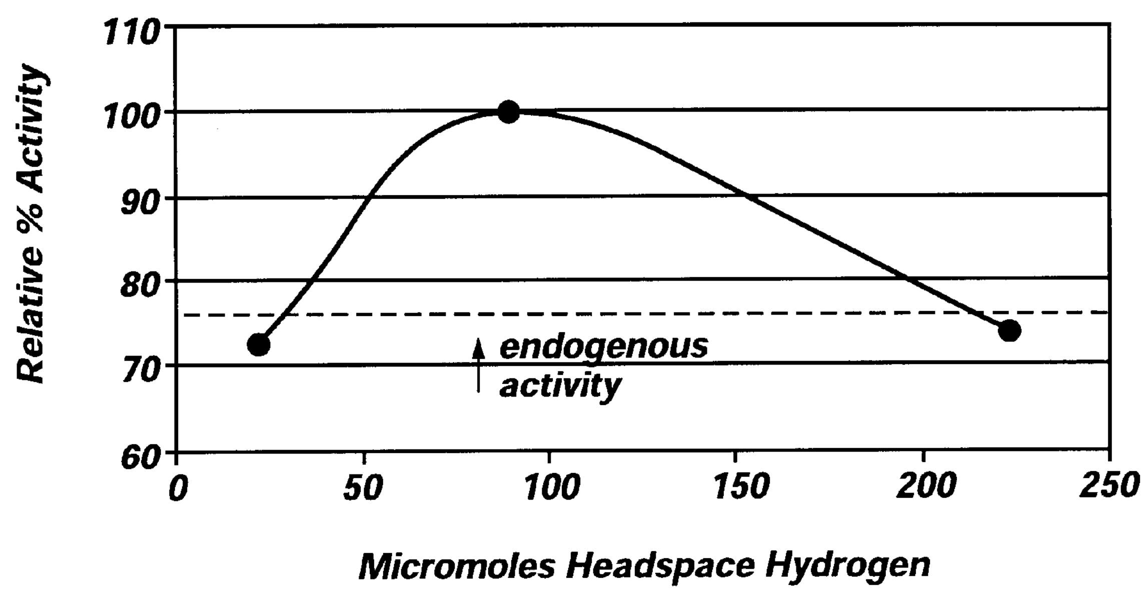
FIG. 5 shows relative hydrogenase activity in reconstituted whole cell enzyme preparation from *M. trichosporium* OB3b cells in 98% (v/v) isooctane as a function of micromoles of headspace hydrogen.

In this example, the procedure of Example 1 was followed except that no formate was added to the reconstituted lyophilized cells. Instead, various concentrations of hydrogen gas were added to the headspace gas composition for assaying hydrogenase activity for regenerating reducing equivalents. FIG. 5 shows the results obtained in a biphasic system containing 98% isooctane. The assay conditions were: t=90 minutes, 150 rpm, 25.5–27.0° C., $V_T$=1000 ml, 45 mmol propylene. These results show stimulation of reconstituted hydrogenase activity over that of endogenous activity. Formate dehydrogenase activity was negligible in this experiment.

EXAMPLE 5

In this experiment *M. trichosporium* OB3b cells were cultured according to the procedure of Example 1 except that a multiphasic reactor system was used, as will be described below. Two problems encountered with the multiphasic (minimal aqueous volume) systems for culturing whole cells are that salt components may become limiting after sufficient cell mass has been generated, and sufficient iron must be supplied in a form that can be utilized by the methanotrophic bacteria. To address these problems, cells were cultured in a multiphasic system containing an aqueous phase, an alkane, and a perfluorocarbon in varying proportions. NSM medium was added at twice the concentration of Example 1. Chelated iron (80 μM) was used to maximize a stable concentration of available iron for maximal sMMO activity.

Table 4 summarizes the compositions of various multiphase matrices. The volumetric aqueous phase content was maintained at 40% (v/v), and hexadecane comprised the balance of the liquid phase.

TABLE 4

| | Volume % | | | |
|---|---|---|---|---|
| Sample No. | Hexadecane | FC77 | FC40 | Aqueous |
| 1 | 56 | 4 | 0 | 40 |
| 2 | 48 | 12 | 0 | 40 |
| 3 | 40 | 20 | 0 | 40 |
| 4 | 56 | 0 | 4 | 40 |
| 5 | 48 | 0 | 12 | 40 |
| 6 | 40 | 0 | 20 | 40 |

After more than two weeks of incubation under 30% (v/v) methane atmosphere, visible cell growth was obtained. Subsamples were then plated on NSM-agarose solid medium. Cell growth was rapid and profuse, with no obvious morphological abnormalities evident by phase contrast microscopy. These results show that cells can be maintained in media containing significant quantities of organic solvents.

We claim:

1. A method for microbial production of an oxygenated derivative of a gaseous methane-monooxygenase substrate comprising:

incubating an immobilized reconstituted lyophilized whole cell enzyme preparation of methanotrophic bacteria containing methane monooxygenase and hydrogenase in a bioreactor, said bioreactor comprising a biphasic liquid phase comprising a major amount of a non-polar, non-aqueous solvent and a minor amount of a polar aqueous medium, a non-aqueous solvent circulation circuit for circulating said non-polar non-aqueous solvent through said bioreactor, and an aqueous medium circulation circuit for circulating said polar aqueous medium through said bioreactor in a counter-current manner as compared to said non-polar, non-aqueous solvent;

continuously dissolving effective amounts of oxygen gas, hydrogen gas, and the gaseous methane-monooxygenase substrate in said non-polar, non-aqueous solvent, wherein said gaseous methane-monooxygenase substrate is readily soluble in said non-polar, non-aqueous solvent and is susceptible to oxidation by said methane monooxygenase to result in the oxygenated derivative thereof, wherein said oxygenated derivative is a polar liquid;

circulating said non-polar, non-aqueous solvent in close proximity to said reconstituted lyophilized whole cell enzyme preparation of methanotrophic bacteria containing methane monooxygenase and hydrogenase such that said methane monooxygenase oxidizes said gaseous methane-monooxygenase substrate into said oxygenated derivative;

circulating said polar aqueous medium in a counter-current manner through said circulating non-polar non-aqueous solvent such that said oxygenated derivative is partitioned into said polar aqueous medium; and removing and recovering said oxygenated derivative from said polar aqueous medium and recycling said non-polar non-aqueous solvent and said polar aqueous medium.

2. The method of claim 1 wherein said oxygenated derivative is propylene oxide and said gaseous methane-monooxygenase substrate is propylene.

3. The method of claim 1 wherein said methanotrophic bacteria are selected from the group consisting of Methylosinus, Methylococcus, Methylomonas, and mixtures thereof.

4. The method of claim 3 wherein said methanotrophic bacteria are *Methylosinus trichosporium* OB3b (ATCC 35070).

5. The method of claim 1 wherein said non-polar non-aqueous solvent comprises isooctane.

6. The method of claim 1 wherein said non-polar non-aqueous solvent comprises hexane.

7. The method of claim 1 wherein said non-polar non-aqueous solvent comprises silicone oil.

8. The method of claim 1 wherein said non-polar non-aqueous solvent comprises hexadecane.

9. The method of claim 1 wherein said non-polar non-aqueous solvent comprises a fluorocarbon.

* * * * *